United States Patent
Fenyö

(10) Patent No.: US 7,661,834 B2
(45) Date of Patent: Feb. 16, 2010

(54) LIGHTING UNIT FOR PRODUCING LINEARLY POLARIZED LIGHT DIRECTED ONTO A TARGET SURFACE

(75) Inventor: Marta Fenyö, Budapest (HU)

(73) Assignee: Polárium Hangulat és Közérzetjavító KFT, Budapest (HU)

(*) Notice: Subject to any disclaimer, the term of this patent is extended or adjusted under 35 U.S.C. 154(b) by 265 days.

(21) Appl. No.: 11/571,740

(22) PCT Filed: Jul. 8, 2005

(86) PCT No.: PCT/HU2005/000075

§ 371 (c)(1),
(2), (4) Date: Jun. 14, 2007

(87) PCT Pub. No.: WO2006/005976

PCT Pub. Date: Jan. 19, 2006

(65) Prior Publication Data

US 2008/0007948 A1    Jan. 10, 2008

(30) Foreign Application Priority Data

Jul. 8, 2004  (HU) ............................. 0400170 U

(51) Int. Cl.
*F21V 9/14* (2006.01)

(52) U.S. Cl. ............... 362/19; 362/97.3; 362/231; 362/249.02; 362/294; 359/487

(58) Field of Classification Search ............. 362/19, 362/231, 235, 249.02, 249.06, 293, 294, 362/373, 97.3; 359/487
See application file for complete search history.

(56) References Cited

U.S. PATENT DOCUMENTS

| | | | | |
|---|---|---|---|---|
| 4,020,336 A | * | 4/1977 | Linder | 362/19 |
| 6,523,978 B1 | * | 2/2003 | Huang | 362/249.06 |
| 7,153,015 B2 | * | 12/2006 | Brukilacchio | 362/555 |
| 7,311,722 B2 | * | 12/2007 | Larsen | 607/88 |
| 2003/0218880 A1 | | 11/2003 | Brukilacchio | |

FOREIGN PATENT DOCUMENTS

| | | |
|---|---|---|
| DE | 20311041 U1 | 11/2003 |
| DE | 10224705 | 12/2003 |
| WO | WO-84/04463 | 11/1984 |
| WO | WO-02/062420 | 8/2002 |

\* cited by examiner

*Primary Examiner*—Stephen F Husar
(74) *Attorney, Agent, or Firm*—Birch, Stewart, Kolasch & Birch, LLP

(57) ABSTRACT

Lighting unit for producing linearly polarized light directed onto a target surface comprising a source unit producing light in the visible spectral range, and an optically translucent polarizing front unit (4) providing protection against external effects. The source unit and the polarizing front unit (4) are placed in a housing (8) in which an electric cable passes through. The source unit (1) contains at least one panel (2) having a number of high intensity LED devices (3) arranged in a predetermined pattern on one of its sides. The polarizing front unit (4) contains at least one optically transparent rigid carrier and a polarizing filter foil applied onto the carrier. The housing (8) keeps the polarizing front unit (4) in a fixed position so that they confine a hermetically closed inner space. The panel (2) is positioned parallel with the polarizing unit (4) within the inner space so that the LED devices (3) face towards the polarizing front unit (4).

26 Claims, 3 Drawing Sheets

LIGHTING UNIT FOR PRODUCING LINEARLY POLARIZED LIGHT DIRECTED ONTO A TARGET SURFACE

The invention relates to a lighting unit for producing linearly polarized light directed onto a target surface, the lighting unit comprises at least a source unit producing light in the visible spectral range and an optically translucent polarizing front unit providing protection against external effects, the source unit and the polarizing front unit are placed in a housing in which an electric cable passes through.

It is known that polarized, especially linearly polarized light is beneficial to vital functions and is capable for strengthening the organism to combat disorders. In case of humans it can be used for general conditioning. In case of animal husbandry it can be used in order to increase yield and to treat certain inflammatory diseases.

Consequently, a compact lighting unit is needed which can be installed easily and is able to emit light with required intensity in the proper direction. Advantageously the units are extendable by simple multiplication of them depending on the purpose and the circumstances.

EP 0,279,002 described an arrangement for producing polarized light where the spectral range of the emitted light is basically found in the UV range. There is no proposal for special use of the polarized light in the visible range.

At the same time U.S. Pat. No. 4,612,604 described a polarizer of the Brewster kind to create biostimulation. The light emission efficiency is, however, not properly handled.

The document WO 9309847 disclosed a device for photometric stimulation of living cells, where diodes produce light in three separate wavelengths. The solution lacks continual emitted light wavelength in a given range, therefore no sufficient effects on the living cells were experienced.

It has been realized that the recently available relatively cheap so called high intensity LED devices with growing light output and improved efficiency are suitable for embodiments of divided units or panels substantially emitting light from a plane in a continuous wavelength range, and may be used for forming a lighting unit according to the object of the invention.

Accordingly, the source unit of the lighting equipment described in the preamble contains at least one panel which has a number of high intensity LED devices arranged in a predetermined pattern on one of its sides. The polarizing front unit contains at least one optically transparent rigid carrier, and a polarizing filter foil applied onto the carrier. At least a portion of the housing is made from heat conductive material, and it keeps the polarizing front unit in a fixed position so that they confine a hermetically closed inner space. The panel is positioned in a fixed way parallel with the polarizing unit within the inner space so that the high intensity LED devices face towards the polarizing front unit.

A detailed description of embodiments of the lighting unit according to the invention will now be disclosed with reference to the accompanying drawings in which.

Figure 1:
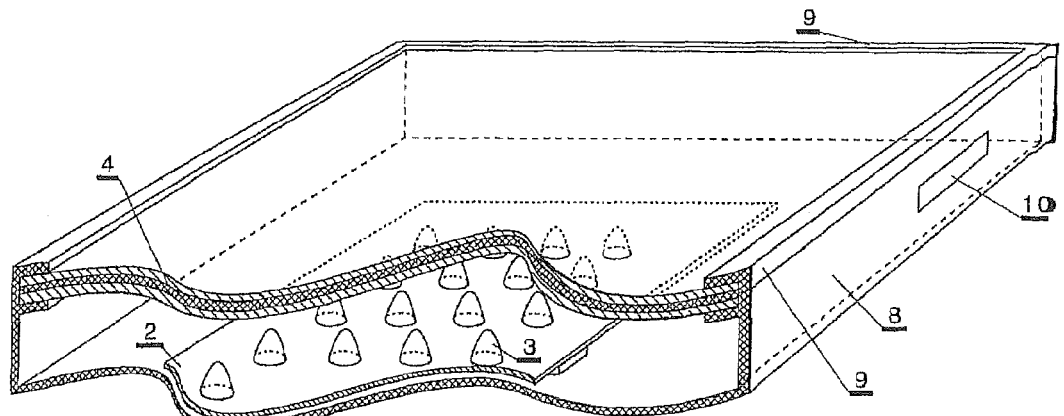
FIG. 1 is a perspective view of a fragment of an exemplary lighting unit according to the invention.

FIG. 1 is a perspective view of a fragment of an exemplary lighting unit according to the invention, in which a source unit 1 producing light in the visible and near infrared spectral range and an optically translucent polarizing front unit 4 providing protection against external effects can be seen. Source unit 1 and polarizing unit 4 are placed in a housing 8. Source unit 1 contains at least one panel 2 which has a number of high intensity LED devices 3 arranged in a predetermined pattern on one of its sides. In FIG. 1 this pattern is a matrix. An electric cable (not shown) passing somewhere through housing 8 supplies energy for LED devices 3. The same source unit 1 may contain a number of separate panels 2 or these panels may be attached to each other in a releasable manner.

Figure 2:
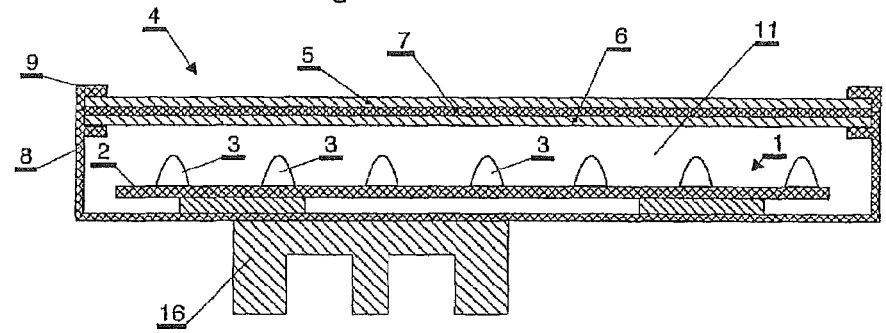
FIG. 2 is a sectional view of the lighting unit of FIG. 1.

According to FIG. 2 the polarizing front unit 4 contains at least one optically transparent rigid carrier 5 and a polarizing filter foil 7 applied onto the carrier 5. At least a portion of housing 8 is made from heat conductive material, for example metal in order to reduce the heat developing during operation. To reduce the heat of the inner space 11 also any other known means, for example heat-insulating paint layer might be proper. Polarizing front unit 4 is fixed to housing 8 by means of a frame 9 so that they confine a hermetically closed inner space 11. Panel 2 is positioned in a fixed way parallel with the polarizing front unit 4 within inner space 11 so that the high intensity LED devices 3 face towards the polarizing front unit 4. Optionally, cooling flange 16 may also be applied at the bottom part of housing 8 in order to reduce heat developing in the inner space 11.

In respect of this invention the term LED devices is used for all high-efficiency light emitting semiconductor devices and structures currently manufactured in mass-production and available in trade. These devices and structures are continuously developed in order to reach higher and higher luminous efficiency. Such devices emit light within the visible and near infrared spectral range in the form of white light which may have different colour temperatures. In the present invention the term LED devices 3 is used in a comprehensive meaning, especially for known high-intensity, high-power LED (Light Emitting Diode) or OLED (Organic Light Emitting Diode) devices. The latter renders possible to use a plane luminous foil which—theoretically—may be cut to an optional size. Also LEP (Light Emitting Polymer) devices may be used. To sum it up, according to the present invention all those devices may be regarded as LED devices 3 which are known as SSL (Solid State Lighting) electronic devices in the state of the art. Current possibilities in trade make dominantly the use of discrete LED devices feasible.

Figure 3:
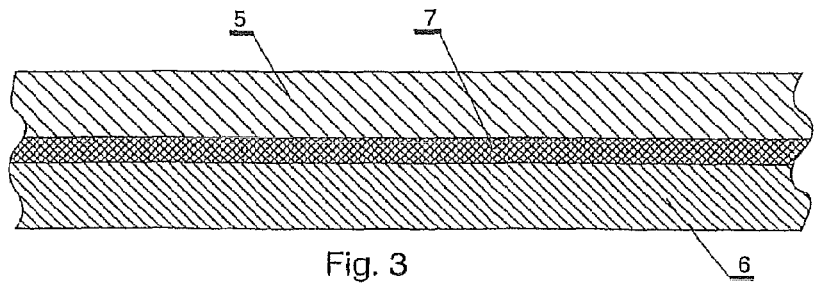
FIG. 3 is a sectional view of a first example embodiment of the polarizing front unit.

FIG. 3 shows the cross-section of a possible structure of the polarizing front unit 4. The optically transparent rigid carrier 5 together with a similar carrier 6 form a sandwich structure surrounding the polarizing filter foil 7. This polarizing filter foil may be applied onto either carrier 5 or carrier 6. Application may be performed by sticking, heat-treatment, etc. It is also possible that polarizing filter foil 7 is simply kept in its place by exertion of a mechanical force. Polarizing filter foils are known and commercially available. Advantageously, the polarizing filter foil 7 is highly transparent, preferably it has a light-transmitting capacity of more than 40%. Advantageously, the carriers 5 and 6 are made of plexi-glass, transparent polycarbonate or similar plastic material, however glass or hardened glass may also be appropriate.

Figure 4:
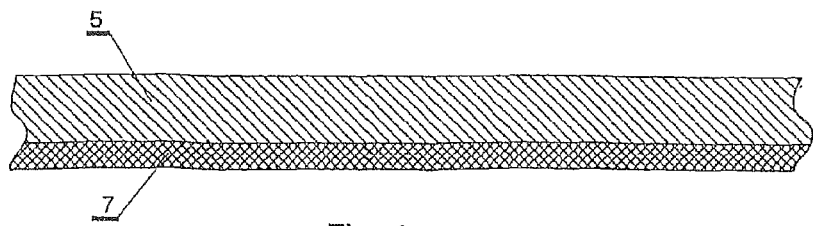
FIG. 4 is a sectional view of a second example embodiment of the polarizing front unit.

According to FIG. 4 only a single carrier 5 is used. In this case polarizing front unit 4 contains a polarizing filter foil 7 applied onto carrier 5 by using one of the applying methods previously described.

Figure 5:
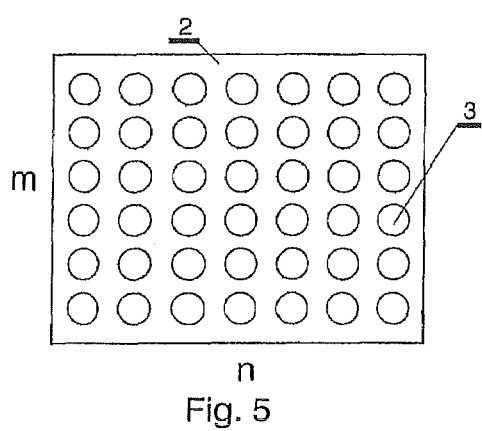
FIG. 5 shows the LED devices arranged in a first pattern.
Figure 7:
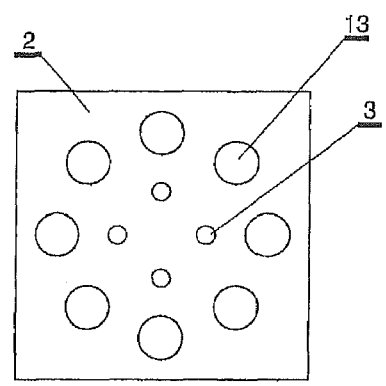
FIG. 7 shows the LED devices arranged in a third pattern.
Figure 6:
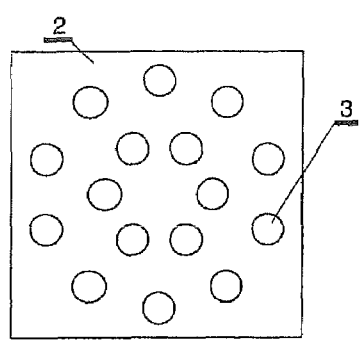
FIG. 6 shows the LED devices arranged in a second pattern.
Figure 8:
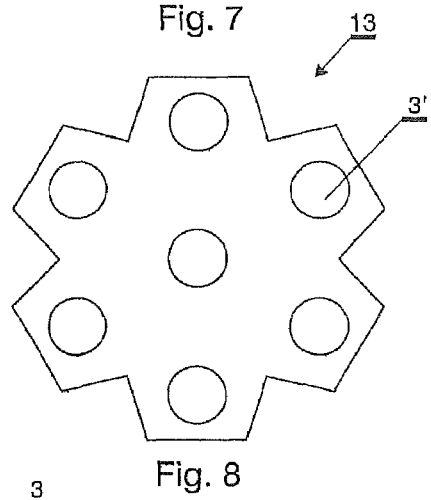
FIG. 8 shows the shape and parts of one of the elements of FIG. 7.
Figure 9:
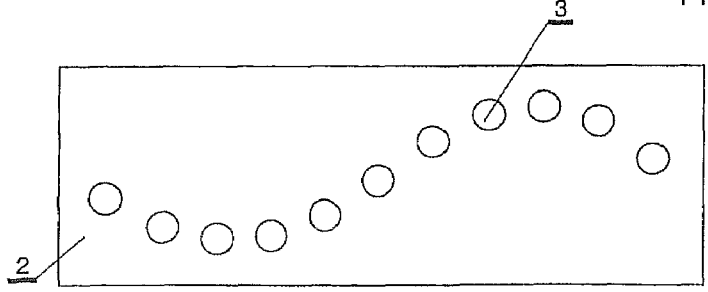
FIG. 9 shows the LED devices arranged in a fourth pattern.
Figure 10:
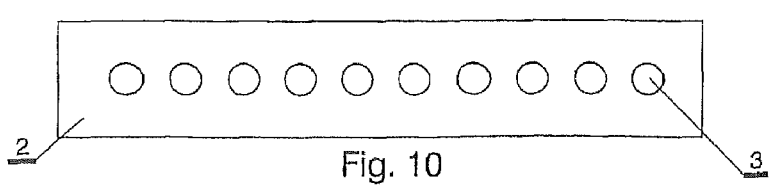
FIG. 10 shows the LED devices arranged in a fifth pattern.

As it was mentioned LED devices 3 are arranged on one of the sides of panel 2 in a predetermined pattern. This pattern may be a matrix containing a number of rows m and columns n as it is shown in FIG. 5 or the LED devices 3 may be arranged concentrically as it can be seen in FIG. 6. Further, the LED devices 3 may be arranged in an undulating line as it is shown in FIG. 9 or they may be distributed along a straight line according to FIG. 10. As it is shown in FIG. 7 the light source may be different in the same pattern. In this case in addition to LED devices 3 compound LED devices 13 containing several LED components 3' arranged in a starlike pattern as shown in FIG. 8 may be used. These LED devices 13 are available in trade. The LED devices 3 and compound LED devices 13 may be arranged in like manner as it is shown in FIG. 6.

Preferably, in certain applications most of the LED devices 3 placed in the lighting unit emit warm white light. However, it is possible that a small number of LED devices 3 emitting coloured light are also applied.

Figure 11:
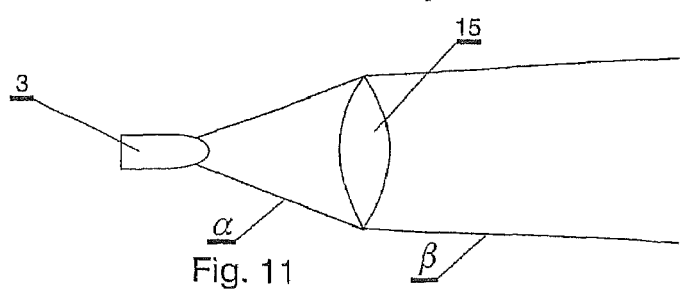
FIG. 11 is a block diagram showing the collimation of the light beams of the LED devices.

It is an object of the lighting unit according to the invention to produce relatively directed linearly polarized light instead of diffused light with divergent beams. For this purpose an additional optical element 15 decreasing the light emitting space angle α of the LED devices 3 may be positioned before the LED devices 3 or at least before some of them. This can be a lens as it is shown in FIG. 11. The original space angle α of the light emitted from LED device 3 is cut down to space angle β by means of the optical element (lens) 15. Space angle β is smaller than space angle α. It proves to be good if the resultant space angle β before the polarizing front unit 4 has an aperture angle of 10-50°. For practical purposes in case of large surfaces the optically transparent rigid carriers 5 or 6 of polarizing front unit 4 may contain a Fresnel lens.

The lighting unit according to the invention can be used for certain therapeutic purposes—not detailed in the present description—if the intensity of the resultant light measured at a distance of 0.5 m from the polarizing front unit 4 is between 5-60 mW/cm². Advantageously this value is between 30-40 mW/cm².

Figure 12:
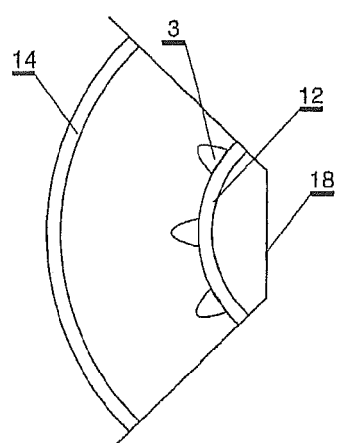
FIG. 12 shows an embodiment of the lighting unit according to the invention when it is bent cylindrically in one dimension.

An alternative embodiment of the lighting unit described with reference to FIG. 1 can be seen in FIG. 12. Panel 12 of the source unit is bent so that it has a convex surface with respect to polarizing front unit 14. Polarizing front unit 14 is bent similarly. In this manner the distance between panel 12 and polarizing front unit 14 is constant. These bendings must be performed in one dimension (in order to guarantee linear polarization) and they result in a cylindrical surface, as it is shown in FIG. 12. The direction of polarization of the polarizing filter foil 7 is parallel with the axis of the cylinder. The shape of the housing 18 is optional, it may be different from the one shown in the Figure. Advantageously, its inner surface is coated with light-reflecting material.

Figure 13:
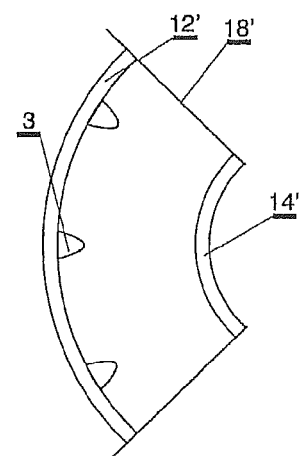
FIG. 13 shows another embodiment of the lighting unit according to the invention when it is bent cylindrically in one dimension.

In another alternative embodiment shown in FIG. 13 the filter and the light source are interchanged, and panel 12' containing LED devices 3 is bent so that it has a concave surface with respect to polarizing front unit 14'. Again, the shape of the housing 18' is optional, it may be different from the one shown in the Figure.

Figure 14:
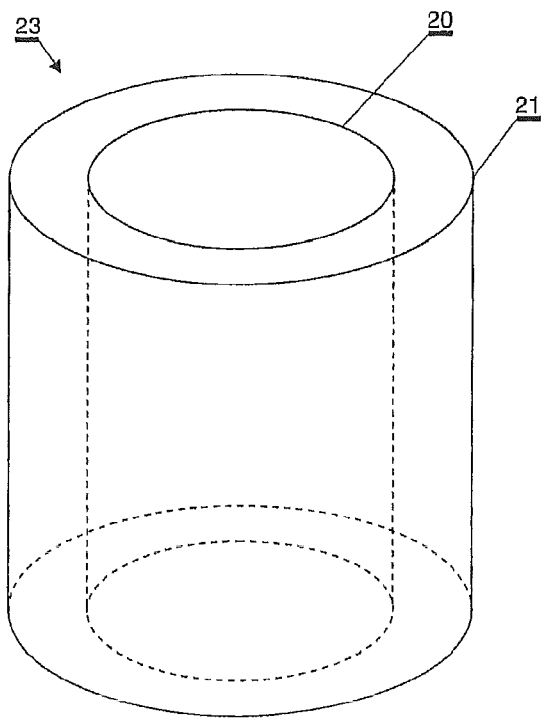
FIG. 14 is a schematic view of a cylindriform lighting unit according to the invention.

An extended version of the embodiments shown in FIGS. 12 and 13 can bee seen in FIG. 14 in which the bendings result in a complete cylinder. Cylinder surfaces 20 and 21 are not designated as panels 12, 12' or polarizing front units 14, 14' indicating by this that they are interchangeable.

Figure 15:
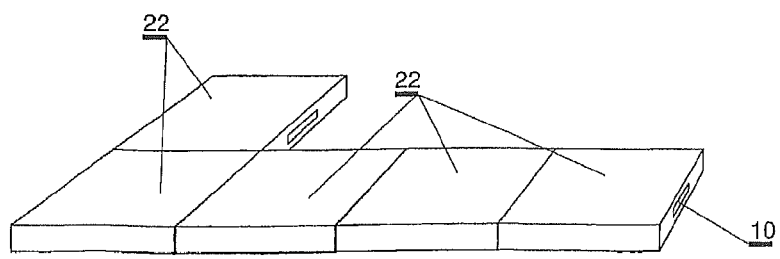
FIG. 15 is a schematic view of an extended lighting unit comprising several units connected to each other.

The lighting unit according to the invention in its entirety may be disc-shaped or parallelepiped. Especially the latter has an advantage that the shape of the individual lighting units makes possible to extend it by further units, i.e. several lighting units can be connected (both mechanically and electrically) to each other easily. In FIG. 15 the side of housing 8 is provided with a mechanical connecting element 10 by means of which a plurality of rectangular lighting units 22 can be connected to each other so that their polarizing front units are in the same plane. Connecting elements 10 may be provided on all four sides of the housing 8 while counterparts are formed on the opposite sides. In this manner extension according to FIG. 15 can be performed easily. Connecting element 10 is also shown symbolically in FIG. 1.

The lighting unit according to the present invention has several advantages, for example in the specific utilization of the enhancement of the productivity of dairy farms. Any other kind of breeding animals can also be a scope of utilisation of the present invention. It can be implemented simply, it is mobile and can be extended easily without the need for changing the already installed units. Further, it does not get overheated in spite of the dust- and vapour-resistant closed housing.

The invention claimed is:

1. A lighting unit for producing linearly polarized light directed onto a target surface, said lighting unit comprises at least a source unit producing light in the visible spectral range and an optically translucent polarizing front unit providing protection against external effects, said source unit and said polarizing front unit are placed in a housing in which an electric cable passes through, characterized in that said source unit contains at least one panel having a number of high intensity LED devices arranged in a predetermined pattern on one of its sides; said polarizing front unit contains at least one optically transparent rigid carrier and a polarizing filter foil applied onto said carrier; at least a portion of said housing is made from heat conductive material, and it keeps said polarizing front unit in a fixed position so that they confine a hermetically closed inner space; said panel is positioned in a fixed way parallel with said polarizing unit within said inner space so that said high intensity LED devices face towards said polarizing front unit and wherein the intensity of the resultant light measured at a distance of 0.5 m from said polarizing front unit is between 5-60 mW/cm².

2. The lighting unit according to claim 1 characterized in that said predetermined pattern is a matrix containing a number of rows (m) and columns (n).

3. The lighting unit according to claim 1 characterized in that said predetermined pattern is composed of concentric circles.

4. The lighting unit according to claim 1 characterized in that said predetermined pattern is an undulating or straight line.

5. The lighting unit according to claim 1 characterized in that said LED devices are compound LED devices containing several LED components arranged in a starlike pattern.

6. The lighting unit according to claim 1 characterized in that said source unit contains a number of panels either separately or attached to each other in a releasable manner.

7. The lighting unit according to claim 1 characterized in that said polarizing front unit contains one optically transparent rigid carrier having a polarizing filter foil applied onto its side facing towards said inner space.

8. The lighting unit according to claim 1 characterized in that said polarizing front unit contains two parallel optically transparent rigid carriers and a polarizing filter foil placed in between said carriers.

9. The lighting unit according to claim 1 characterized in that said optically transparent rigid carrier is made of plexiglass.

10. The lighting unit according to claim 1 characterized in that said optically transparent rigid carrier is made of glass.

11. Lighting The lighting unit according to claim 1 characterized in that said optically transparent rigid carrier is made of hardened glass.

12. The lighting unit according to claim 1 characterized in that at least a portion of said panel is made from heat conductive material.

13. The lighting unit according to claim 12 characterized in that said heat conductive material is metal.

14. The lighting unit according to claim 1 characterized in that said polarizing filter foil has a light transmitting capacity of more than 40%.

15. The lighting unit according to claim 1 characterized in that the majority of said LED devices included in said lighting unit emit warm white light.

16. The lighting unit according to claim 1 characterized in that the minority of said LED devices placed in said lighting unit emit coloured light.

17. The lighting unit according to claim 1 characterized in that an additional optical element is positioned at least before some of said LED devices in order to decrease the light emitting space angle ($\alpha$) of said LED devices.

18. The lighting unit according to claim 1 characterized in that a resultant space angle ($\beta$) before said polarizing front unit has an aperture angle of 10-50°.

19. The lighting unit according to claim 1 characterized in that the intensity of the resultant light measured at a distance of 0.5 m from said polarizing front unit is between 30-40 mW/cm$^2$.

20. The lighting unit according to claim 1 characterized in that said source unit and said polarizing front unit are bent cylindrically in one dimension, and the direction of polarization of said polarizing filter foil is parallel with the axis of the cylinder.

21. The lighting unit according to claim 20 characterized in that it is cylindriform.

22. The lighting unit according to claim 1 characterized in that it is disc-shaped.

23. The lighting unit according to claim 1 characterized in that it is rectangular.

24. The lighting unit according to claim 1 characterized in that the side of said housing is provided with a mechanical connecting element for connecting a number of lighting units to each other so that their polarizing front units are in the same plane.

25. The lighting unit according to claim 1 characterized in that said housing is provided with a cooling flange.

26. The lighting unit according to claim 1 characterized in that the inner surface of said housing is coated with light reflecting material.

* * * * *